United States Patent [19]

Blyler, Jr. et al.

[11] Patent Number: 4,834,496
[45] Date of Patent: May 30, 1989

[54] OPTICAL FIBER SENSORS FOR CHEMICAL DETECTION

[75] Inventors: Lee L. Blyler, Jr., Basking Ridge; Leonard G. Cohen, Berkeley Heights; Robert A. Lieberman, New Providence; John B. MacChesney, Lebanon, all of N.J.

[73] Assignee: American Telephone and Telegraph Company, AT&T Bell Laboratories, Murray Hill, N.J.

[21] Appl. No.: 53,230

[22] Filed: May 22, 1987

[51] Int. Cl.$^4$ .............................................. G02B 6/02
[52] U.S. Cl. ............................ 350/96.29; 250/231 R; 250/227; 350/96.33; 436/805
[58] Field of Search ............... 436/805, 127, 524, 527, 436/528, 531, 535; 250/227, 231 R; 356/73.1, 445; 350/96.1, 96.15, 96.16, 96.17, 96.29, 96.30, 96.33, 96.34

[56] References Cited

U.S. PATENT DOCUMENTS

| | | | |
|---|---|---|---|
| 4,050,895 | 9/1977 | Hardy et al. | 436/805 X |
| 4,200,110 | 4/1980 | Peterson et al. | 128/634 |
| 4,368,047 | 1/1983 | Andrade et al. | 436/805 X |
| 4,371,897 | 2/1983 | Kramer | 250/227 X |
| 4,447,546 | 5/1984 | Hirschfeld | 250/227 X |
| 4,511,209 | 4/1985 | Skutnik | 350/96.34 |
| 4,513,087 | 4/1985 | Giuliani et al. | 436/96 |
| 4,558,014 | 12/1985 | Hirschfeld et al. | 436/527 |
| 4,560,248 | 12/1985 | Cramp et al. | 350/96.34 |
| 4,582,809 | 4/1986 | Block et al. | 436/805 X |
| 4,666,672 | 5/1987 | Miller et al. | 436/126 X |
| 4,710,353 | 12/1987 | Tanaka et al. | 350/96.29 X |

FOREIGN PATENT DOCUMENTS 211587 2/1987 European Pat. Off. ......... 350/96.29

OTHER PUBLICATIONS

*Optical Fiber Telecommunications*, eds. S. E. Miller and A. G. Chynoweth, Academic Press, New York, New York, Chapters 3, 9, 11, 14, 16 and 18 (1979).

"Numerical Prediction of Fiber Transmission Characteristics from Arbitrary Refractive-Index Profiles", Applied Optics, vol. 21, No. 4, W. L. Mammel and L. G. Cohen, pp. 699-703, Feb. 15, 1982.

"Preparation of Plastic Optical Fibers", *Review of the Electrical Communication Laboratories*, vol. 32, No. 3, T. Kaino, M. Fujiki and K. Jinguji, pp. 478-488 (1984).

Primary Examiner—William L. Sikes
Assistant Examiner—Frank González
Attorney, Agent, or Firm—Bruce S. Schneider

[57] ABSTRACT

Distributed region optical sensors for chemical detection are provided by utilizing optical fiber technology. A core is provided with a surrounding region that is permeable to the chemical to be detected. A composition whose optical characteristics are altered upon interaction with the chemical to be detected is provided within the permeable material. This change in optical characteristics allows chemical detection through detection of light guided by the fiber.

31 Claims, 2 Drawing Sheets

MULTIMODE

SINGLE MODE

MULTIMODE

SINGLE MODE

OPTICAL FIBER SENSORS FOR CHEMICAL DETECTION

TECHNICAL FIELD

This invention relates to chemical detection and, in particular, chemical detection done by optical techniques.

BACKGROUND OF THE INVENTION

Chemical detection is a pressing necessity for many applications. Most chemical sensors are small area sensors, i.e., sensors with responsive regions having small lateral dimensions. These sensors are based on changes in characteristics such as electrochemical and optical properties. For example, as discussed in Peterson et al. U.S. Pat. No. 4,200,110 issued Apr. 29, 1980, a small area chemical sensor using fiber optics is made by enclosing a material that reacts with the chemical to be sensed and attaching this package to the end of an optical fiber. The material in the enclosure is chosen so that upon interaction with the chemical to be sensed it changes its optical properties. Thus, upon reaction, guided light entering the package interacts with the sensitive material and the presence of the chemical is detectable as a change in optical absorbance or fluorescence at one or more wavelengths. This change is observed in the light guided back along the fiber.

Some important applications require rapid response, i.e., response in peroids shorter than 1 minute from time of chemical release. For example, it is often desirable to continuously monitor for the presence of undesirable gases to ensure worker safety. Alternatively, it is often necessary to monitor for gases which indicate a malfunctioning chemical process. Small area sensors are limited by the transit time from the source of gas to the responding area of the sensor. Even the placement of a reasonable number of small area sensors is generally not entirely satisfactory. Despite the severe response limitations of small area sensors in distributed region applications, they have nevertheless been utilized for lack of a better alternative.

Attempts to expand the response region of sensors have led to undesirable results. In one approach (U.S. Pat. No. 4,560,248 issued Dec. 24, 1985) a relatively short region of an optical fiber core having the solid cladding removed was made porous. This porous area was then filled with a dye whose optical properties changed upon interaction with the chemical to be detected. However, the bare core of the sensor is susceptible to external damage, e.g., scratches, resulting in breakage. Additionally, the desired signal is rapidly attenuated by scattering at the porous glass/core interface. Thus, such a sensor is not robust and the production of a porous core over an extended region severly complicates fabrication and detection.

As described by Giuliani in U.S. Pat. No. 4,513,087 issued Apr. 23, 1985, a second approach to fabricating a distributed region sensor involves a capillary tube coated with a comparison that changes optical absorption properties upon interaction with the chemical to be detected. This change, in turn, induces a detectable wavelength dependent change in the intensity of the light guided by the annulus of the capillary tube. A capillary tube rather than a solid rod was used, according to Giuliani, to ensure sufficient interaction between the chemically sensitive composition and the guided light. Clearly, however, this configuration is quite susceptible to breakage, is susceptible to contamination, and is not easily configured along a curvilinear path. Thus, a flexible, robust distributed chemical sensor that lends itself to expedient fabrication has not been reported.

SUMMARY OF THE INVENTION

A robust, distributed region chemical sensor, i.e., one with a total responsive path length greater than one-half meter preferably greater than one meter, is producible utilizing an optical fiber, i.e., an optical waveguide having a core diameter less than 500 $\mu$m for core materials with Young's modulus greater than $1 \times 10^6$ psi ($7 \times 10^9$ Pa) and less than 1 mm for core materials with moduli less than $1 \times 10^6$ psi ($7 \times 10^9$ Pa). A fiber core is provided with a coating of lower refractive index to provide a cladding. The coating is also chosen to have a Young's modulus greater than 15 psi ($10^5$ Pa) but less than $1.5 \times 10^4$ psi ($10^8$ Pa) to avoid breakage. The cladding either contains, encloses, or is surrounded by a chemically sensitive composition.

Chemical detection is possible by many expedients resulting in a change in the light guided by the fiber. For example, light guided in the core interacts through its evanescent field with the chemically sensitive composition, e.g., a dye. If the dye is induced to fluoresce by light of appropriate wavelength propagating through the core and if the fluorescence is then changed, e.g., quenched, by interaction with the chemical to be detected, the intensity change of the fluorescence coupled into the core is detected as guided light. Alternatively, if the optical absorbance of the dye changes upon interaction, e.g., reaction, the intensity of light at the appropriate wavelength guided by the fiber correspondingly changes and is easily detected.

Other, more complicated schemes are also possible. For example, light that induces fluorescence in the cladding is provided by a source external to the fiber that transversely illiminates the senstive material. The resulting fluorescence is coupled to guided modes in the core through evanescent field interactions. A change in fluorscence, associated with the interaction of the sensitive composition with the chemical to be sensed, is detected as a change in the output intensity of the guided fluorescence. Alternatively, a chemically sensitive composition in the cladding interacts with the evanescent field of guided light or with light from an external source to provide a fluorescence which is augmented or quenched by the presence of the chemical to be sensed. This fluorescence, in turn, causes a second dye or combination of dyes present in the core and having appropriate wavelength response to also fluoresce. Light from this second fluorescence is guided by the fiber. Thus, a substantial change in guided fluorescence intensity indicates the presence of the chemical to be detected. In this situation with an external exciting source, since coupling to guided modes through the evanescent field is not required, the sensitive composition need not be in the cladding but need only be close enough to the core so that a change in optical properties affects the light guided by the fiber.

DETAILED DESCRIPTION

As discussed, the inventive chemical sensors involve an optical fiber having a core, e.g., a glass or a plastic core, with a relatively low modulus, permeable coating which is the cladding, which includes the cladding or which is present in addition to the cladding. The core should generally have a diameter less than 500 μm for core materials with Young's modulus greater than $1 \times 10^6$ psi ($7 \times 10^9$ Pa) and 1 mm or less for core materials with Young's modulus less than $1 \times 10^6$ psi ($7 \times 10^9$ Pa) to allow the fiber to be easily routed. The cladding and, if present, additional coating material should have a modulus in the range 15 psi ($10^5$ Pa) to $1.5 \times 10^4$ psi ($10^8$ Pa). For materials having a modulus larger than $1.5 \times 10^4$ psi the diffusivity of chemicals to be sensed generally becomes too small while coatings have a modulus less than 15 psi result in poor mechanical integrity. Additionally, to ensure light guiding in the core, the cladding should have a refractive index that is smaller than that of the core. For example, for silica cores, cladding materials such as dimethylsiloxane resins and fluorinated elastomers provide the appropriate modulus, permeability and refractive index.

Figure 2:
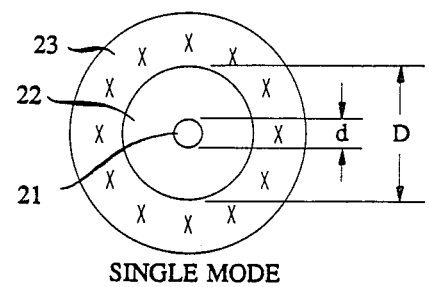
Figure 4:
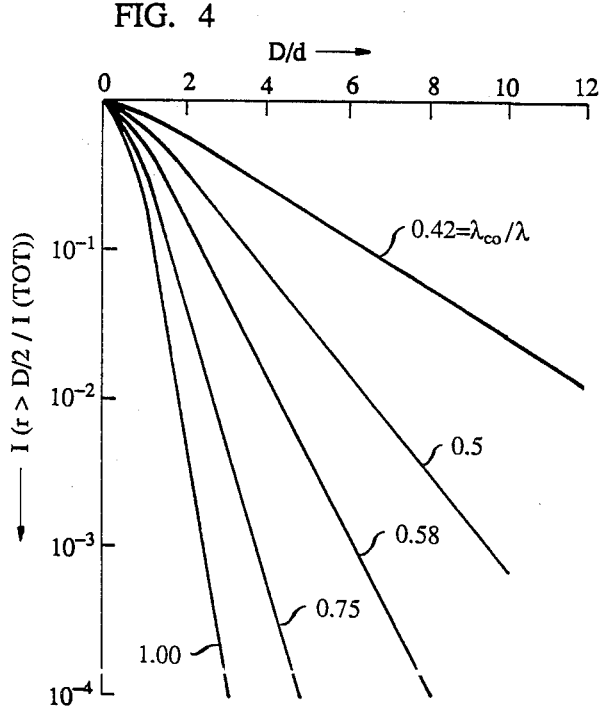

Additionally, it is possible to employ a core that supports either multimode or single mode guided transmission. The production of typical core/cladding refractive index differences in the range 0.3 to 12 percent with core profiles suitable for multimode or single mode guiding is appropriate (see, for example, Miller and Chynoweth, *Optical Fiber Telecommunications,* Academic Press, New York, Chapter 3 (1978)). A single mode embodiment is illustrated in FIG. 2. It has a core 21 (typically a glass core, e.g., germania silicate); a cladding, 22 (typically a glass, e.g., silica or fluorosilicate); and is surrounded by a low modulus permeable second cladding, 23 (containing the chemically-sensitive material) with a refractive-index equal to that of the glass cladding. The cladding, 22, causes less attenuation than the polymer cladding, 23, and therefore serves as a barrier between the low-loss core and the higher loss polymer. The plot in FIG. 4 shows the ratio, $\bar{I}$, between the light power in the polymer cladding $I(r>D/2)$ and the total propagating power, $I(tot)$.

$$\bar{I} = \left( \frac{I(r > D/2)}{I(tot)} \right)$$

versus the cladding-to-core diameter ratio, $D/d$. The variable parameter is $\lambda_{co}/\lambda$ where $\lambda_{co}$ (cut-off wavelength) is the shortest wavelength for single mode transmission. The curves were calculated by computer analysis as reported by W. L. Mammel and L. G. Cohen, "Numerical Prediction of Transmission Characters from Arbitrary Refractive-Index Profiles," *Applied Optics*, 21, pp. 699-703 (1982). Thus, for a coating containing oxazine 750 perchlorate (an ammonia sensitive dye) if $D/d = 12$ and $$\frac{\lambda_{co}}{\lambda} = 0.42$$

then $\bar{I}$ is approximately 0.01 and the resultant loss due to the polymer would be approximately 1 dB/Km in the presence of $NH_3$ and 5 dB/Km in the presence of air.

These losses are approximately 100 times lower than that obtained if the chemically sensitive material were in the cladding adjacent to the core. Thus, improved transmission is obtained relative to a fiber with the chemically sensitive material adjacent to the core at the cost of a reduction in sensitivity per fiber length. If this trade-off is not desirable, it is possible to introduce the chemically sensitive compound into the cladding adjacent to the core.

The chemical to be detected reaches the chemically sensitive composition by diffusion through at least a portion of the cladding or coating surrounding the cladding. It appears that such diffusion would significantly delay response time, and thus defeat the purpose of a distributed sensor. Contrary to these expectations, if the cladding or coating material containing the chemically sensitive compound has a typical thickness, i.e., thickness in the range 25 to 50 μm and has a diffusivity greater than $10^{-7}$ cm$^2$/second, then undue response time delay does not occur.

The chemically sensitive composition in introduced either around the cladding, into the cladding or at the cladding/core interface. (The cladding, for purposes of this application, is considered all material surrounding the core of lower refractive index than that of the core and with a thickness that includes 99.99 percent of the evanescent field penetration.) A convenient expedient for introducing the chemically sensitive composition is to mutually solvate the material in the precursor for the polymer cladding and/or precursor for the polymer coating around the cladding. For example, a compound such as 9,10-diphenylanthracene that is chemically sensitive to oxygen is incorporated into a poly(dimethylsiloxane) resin formulation. A core or core/cladding structure is then coated with the resin and the coating is cured by conventional techniques such as ultraviolet or heat curing. As a result the cladding and/or coating around the cladding includes the chemically sensitive material. Alternatively, it is possible to coat the core with the chemically sensitive compound and then, in turn, cover this coated core with cladding material. As discussed, when it is not necessary to couple to guided modes through the evanescent field, it is possible to put the chemically sensitive composition outside the cladding, e.g., in turn, coating a permeable polymer containing the composition onto the cladding. However, the region containing the chemically sensitive material should not be encapsulated by a material that significantly impedes the diffusive transport of the chemical to be sensed.

The chemically sensitive compound is chosen so that it undergoes a change in optical properties upon interaction, e.g., reaction, with the chemical to be detected. For example, 9,10-diphenylanthracene, oxazine 750 perchlorate and orthotolidine interact with oxygen, ammonia and chlorine respectively. The first interaction involves molecular energy transfer that quenches fluorescence while the latter two involve reactions that cause a change in optical absorption. For reasonable response times, it is desirable that these interaction be relatively efficient, i.e., at least 10 percent of chemically sensitive compound contacted by the chemical to be detected is affected to produce an optical change within 1 minute of the contact. A variety of changes in optical properties is acceptable. For example, it is possible for the chemically sensitive compound upon interaction to become more optically absorbing, less optically absorbing, more intensely fluorescent, less intensely fluorescent, more highly scattering or less highly scattering. The primary criterion is that upon interaction a change in optical property is produced that in the particular configuration of the sensor causes a change in the light guided by the fiber.

Many mechanisms are available to allow the chemically sensitive compound to affect the light guided in the core. Exemplary of such interaction is the use of a chemically sensitive compound in the cladding that undergoes a change in fluorescence upon interaction with the substance to be detected. Light guided in the core is chosen to have a wavelength that excites the fluorescence of the sensitive composition. Thus, the evanescent field of the guided light induces the fluorescence and the resulting fluorescent light is coupled through the evanescent field into the core. Another mechanism for coupling to core guided modes (bound modes) occurs through scattering. Refractive (leaky) modes also convey fluorescence although along a shorter distance. Core guided modes excited by evanescent field coupling, or by coupling through scattering, and refractive modes are both acceptable methods for bringing light to the point of optical detection. The resulting guided fluorescence is easily detected and differentiated (if desired) from the guided excitation light by utilizing a wavelength sensitive detector, e.g., a system including a diffraction grating and/or filter.

In another embodiment for detection involving an indirect mechanism, a sensitive material that reacts with the chemical to be detected is present in the cladding. Compositions such as 9,10-disphenylanthracene and hydroxypyrene trisulfonic acid that respectively interact with entities such as oxygen and $H^+$ ions are chosen so that fluorescence excited by the evanescent field of light guided by the core is quenched upon interaction. A second fluorescent material is incorporated into the core by expedients such as doping a glass core during preform manufacture or by mixing with the precursor for a polymer core. This material is chosen so that it fluoresces upon interaction with the fluorescence from the chemically sensitive compound, i.e., its excitation band overlaps the emission band of the chemically sensitive compound surrounding the core. This fluorescence is guided by fiber and ultimately detected. An alternative to using guided modes to excite fluorescence involves employing an external source that transversely illuminates the fiber. In this embodiment, the chemically sensitive material is incorporated at the core/cladding interface, in the cladding, or in a coating surrounding the cladding. Examples of materials which are suitable for use as fluorescent materials in the core are perylene which has an excitation spectrum overlapping the emission spectrum of 9,10-diphenylanthracene, and rubrene, which has an excitation spectrum overlapping the emission spectrum of hydroxypyrene trisulfonic acid.

In the case of a chemically sensitive compound enclosed by the cladding or a surrounding coating, that upon interaction, changes (1) fluorescence or (2) opacity (through, for example, scattering), the electromagnetic radiation that induces the fluorescence or that is scattered need not be guided light. A source of light external to the fiber is made incident on the cladding. (This source need only illuminate regions in which response is desired.) The wavelength of this light is chosen so that it is not strongly absorbed or scattered in the cladding except by the chemically sensitive material. The resulting fluorescence or scattered light then, at least in part, is guided by the fiber.

A wide variety of detectors are suitable for observing the change in optical properties, e.g., silicon p-i-n photodectors, silicon avalanche detectors, phototransistors and/or photomultiplier tubes. Suitable optics for directing the guided light emanating from the fiber to the detector are fully described in Miller and Chynoweth, supra, Chapter 18. A wide variety of sources for the guided light is also described in Miller and Chynoweth, supra, Chapter 16. (If continuous illumination causes bleaching of the chemically sensitive material, it is advantageous to employ a pulsed source with a low duty cycle to reduce this bleaching.) Suitable wavelengths are generally in the wavelength range 200 nanometers to 1500 nanometers. Choosing a suitable wavelength for a particular optical change is easily accomplished by taking an optical absorption of fluorescence excitation spectrum of the chemically sensitive material in the presence of varying amounts of the substance to be sensed to determine wavelengths associated with optical changes adequate for detection. In the case of scattering, a measurement on a control sample is easily performed to determine an appropriate wavelength for a particular scattering medium. Suitable optics for launching the light into the fiber is described in Miller and Chynoweth, supra, Chapter 11.

The application of the cladding onto an optical fiber core and/or coating the cladding itself is accomplished by conventional optical fiber fabrication procedures. The core is, in one embodiment, drawn from a preform by the conventional procedures described in Miller and Chynoweth, supra, for glass and extruded for polymer cores as described by T. Kaino et al., *Review of the Electrical Communication Laboratories*, 32, 478 (1984). Coating of the drawn core or fiber is also accomplished by conventional techniques such as die application that is described in Miller and Chynoweth, supra, Chapter 9.

It is not necessary that a single fiber sensor be employed. It is possible to bundle fibers or splice them together serially. In the former case by employing fibers with different chemically sensitive compositions, a body that is responsive to a plurality of chemicals is formed or if the same sensitive material is employed sensitivity is enhanced. In the latter situation widely spaced distributed sensors are advantageously connected by splicing low loss fiber between them. (Splicing techniques are described in Miller and Chynoweth, supra, Chapter 14.) It is also possible to increase sensitivity by coiling the fiber so that a longer length occupies a given area. For purposes of this invention, the coiled fiber even though occupying a smaller area, is still considered a distributed sensor.

The following examples are illustrative of configurations for sensors of the invention.

EXAMPLE 1

An oxazine 750 perchlorate in methanol solution was made with a concentration of approximately 10 grams per liter. A sufficient amount of the methanol/dye solution was introduced into a silicone acrylate formulation (DeSolite 114E a proprietary product of DeSoto, Incorporated) to produce a 0.2 percent by weight dye concentration. The composition containing the dye was placed in an open cup coating applicator. The applicator was positioned on a fiber draw tower at a distance of approximately 3 meters from the fiber drawing furnance.

Figure 1:
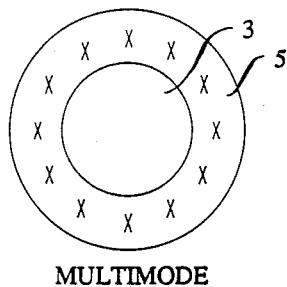
FIGS. 1 and 2 are illustrative of fiber configurations useful in the invention.

An undoped silica quartz rod (Suprasil 2, a product of Heraeus-Amersil) was drawn at a speed of 0.9 m/sec into a fiber core having a diameter of approximately 125 microns. The fiber core was routed through the dye-containing composition in the applicator and through an orifice at the bottom of the applicator which produced a coating having an outside diameter of 230 microns. The coating was then cured by passing the coated fiber in proximity to a UV lamp manufactured by Fusion Systems, Incorporated. At the draw speed employed this lamp produced a UV dose of approximately 1 Joule per square centimeter in the 300 to 400 nm spectral range. The fiber was then wound on a drum. The process was continued until several hundred meters had been drawn. This yielded a multimode fiber (FIG. 1) with core, 3, and cladding, 5.

To produce a control sample the same procedure was followed except the dye was omitted from the silicone acrylate resin. The spectral loss for both the control sample and the dye-containing sample were measured by comparing the light intensity transmitted through a long length of fiber to that transmitted through a relatively short length. (This technique is fully described in Miller and Chynoweth, supra, Chapter 11, and is referred to as the cutback technique.) For the control fiber the long length was approximately 100 meters and the short length was 2 meters. For the dye-containing fiber the long length was 52 meters and the short length was 2 meters. The spectral loss of the dye-containing fiber peaked at 665 nm and was higher relative to the control by approximately 40 dB per kilometer. (This shift indicated the level of additional scattering loss.)

Figure 3:
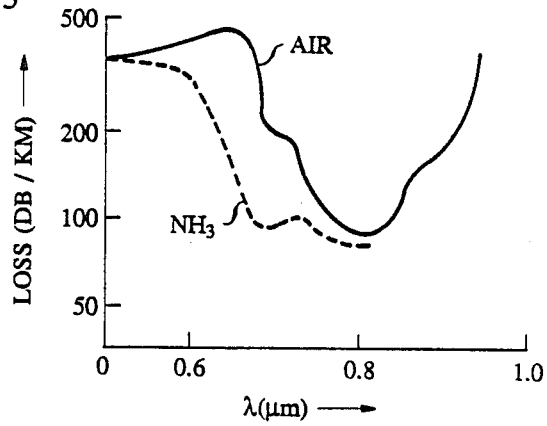
FIGS. 3 and 4 are illustrative of results obtained with the subject invention.

A 12.9m length of dye-containing fiber was placed in a one gallon closed container with ends exiting the container and extending to the spectral loss test set. The internal volume of the container was continuously purged with air. The loss spectrum of the fiber was measured and was as shown in FIG. 3. Subsequently, light at a wavelength of 665 nm was launched into one end of the fiber and the light output at the other end was continuously monitored. The air flow was terminated and the container was then purged with 100 percent anhydrous ammonia. The intensity of light exiting the fiber at a wavelength of 665 nm was measured as a function of time starting at the introduction of ammonia and continuing for approximately 500 seconds. Measurable changes in the observed intensity commenced approximately 7 second after introduction of ammonia. When the observed optical change reached equilibrium the total loss change was approximately 360 dB per kilometer. Approximately 90 percent of the change occurred within the first 40 seconds. The loss spectrum for the fiber equilibrated in the presence of ammonia was measured and is shown in FIG. 3.

EXAMPLE 2

Figure 5:
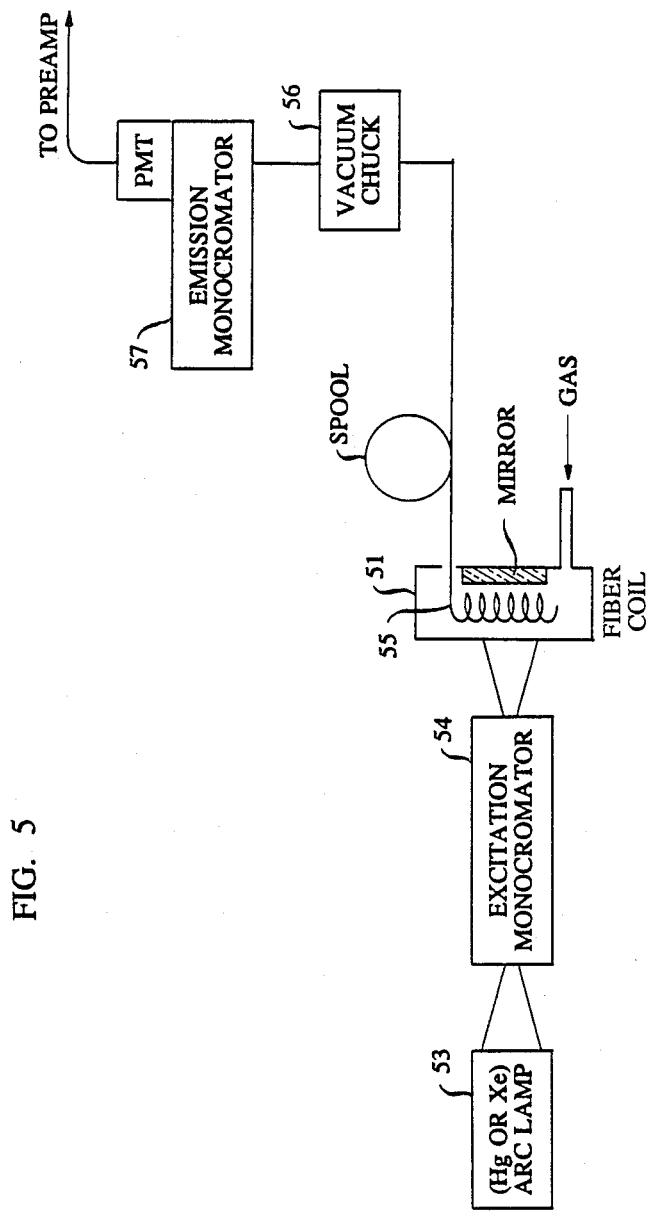
FIG. 5 is illustrative of an apparatus suitable for making optical measurements associated with the invention.

The fabrication procedure of Examlpe 1 was followed except 9,10-diphenylanthracene (9,10-d) was employed as the chemically sensitive material rather than oxazine 750 perchlorate. To incorporate the 9,10-d into the cladding a 2 percent solution was made in toluene and then this solution was mixed with silicone resin (Sylgard 184, a proprietary product of Dow Corning Corporation). To form this mixture the dye solution was first mixed with the silicone base and then, just before the mixture was placed in the coating applicator, the crosslinking and catalyst components of the Sylgard resin were added. The final concentration of the dye in the silicone composition was 0.1 weight percent. The curing of the resin after coating was accomplished by passing the coated fiber through a quartz tube (approximately 16 mm outside diameter, 14 millimeters inside diameter, and 33 centimeters in length) placed below the coating applicator. A current was passed through a platinum wire wound around the tube to produce a temperature of approximately 500° C. Measurement was done utilizing the apparatus shown in FIG. 5. Basically, light from a discharge arc lamp, 53, as introduced into a monochromator, 54, to illuminate the fiber, 55, from the side with light with a relatively narrow spectral range. The output end of the fiber was held in a vacuum chuck, 56, and light emanating from the fiber was directed into the slit of the second monochromator, 57, and detected by a photomultiplier. (The slit width was approximately 150 micrometers.)

The excitation spectrum was measured utilzing a xenon arc lamp light source. The excitation monochromator was scanned through a wavelength range of 330 nm to 410 nm, and the intensity recorded while the emission monochromator was held at a wavelength of 430 nm. Peaks were observed at approximately 370 nm and at approximately 390 nm. In a similar manner the emission spectrum was measured utilizing an arc lamp light source and holding the excitation monochromator at a wavelength of 367 nm. The emission monochromator was scanned between 380 nm and 600 nm. Peaks were observed at approximately 410 nm and 430 nm.

To test oxygen response, a mercury arc lamp was utilized, the excitation monochromator was set at 367 nm, and the emission monochromator was set at 430 nm. The container, 51, surrounding the fiber was initially filled with nitrogen. This nitrogen atmosphere was then replaced with air. A measurable drop in fluorescence was observed within 1 second and more than 90 percent of the total change was observed within 5 seconds of the introduction of the air. By increasing the concentration of the oxygen in the container a corresponding decrease in the observed emission occurred. By increasing the illuminated length of fiber a proportional increase in the output signal was observed although calculations indicate saturation of this effect occurs at approximately 18 meters.

What is claimed is:

1. A distributed chemical sensor comprising an optical fiber with a responsive path length greater than ½ meter, said optical fiber comprising (1) a core and (2) a coating which comprises (A) a cladding adjacent to said core having a refractive index lower than said core and (B) a material that undergoes an otpcial change upon interaction with said chemical, wherein said coating over said responsive path is essentially continuous and is permeable to said chemical, and wherein said optical change is detectable in a change of property of the light guided by said fiber.

2. The sensor of claim 1 wherein said coating comprises a cladding.

3. The sensor of claim 2 wherein said sensitive material comprises a composition chosed from the group consisting of 9,10-diphenylanthracene and oxazine 750 perchlorate.

4. The sensor of claim 1 wherein said coating comprises a silicone acrylate.

5. The sensor of claim 1 wherein said sensitive material comprises a composition chosen from the group consisting of 9,10-diphenylanthracene and oxazine 750 perchlorate.

6. The sensor of claim 1 wherein said core includes a fluorescent material.

7. The sensor of claim 1 wherein said core comprises a glass.

8. The sensor of claim 1 wherein said core comprises a polymer.

9. The sensor of claim 1 wherein said fiber comprises a single mode fiber.

10. The sensor of claim 1 wherein said fiber comprises a multimode fiber.

11. A distributed chemical sensor comprising a plurality of fibers of claim 1.

12. A distributed chemical sensor comprising a plurality of fibers of claim 1 serially spliced together.

13. An apparatus comprising the fiber of claim 1, a source of light that is capable of illuminating the chemically sensitive material of said fiber and a means of detecting changes in light guided in said fiber.

14. A distributed chemical sensor comprising an optical fiber, said optical fiber comprising (1) a core and (2) a coating which comprises (A) a cladding adjacent to said core having a refractive index lower than said core and (B) a material that undergoes an optical change upon interaction with said chemical, wherein said coating over said responsive path is essentially continuous and is permeable to said chemical, and wherein said optical change is detectable in a change of property of the light guided by said fiber wherein a non-permeable cladding is between said core and said coating.

15. A distributed chemical sensor comprising an optical fiber, said optical fiber comprising (1) a core and (2) a coating which comprises (A) a cladding adjacent to said core having a refractive index lower than said core and (B) a material that undergoes an optical change upon interaction with said chemical, wherein said coating over said responsive path is essentially continuous and is permeable to said chemical, and wherein said optical change is detectable in a change of property of the light guided by said fiber wherein said sensitive material is located at said core/coating interface.

16. A process for determining the presence of a chemical over a distributed region, said process comprising the steps of (A) subjecting to an environment an optical fiber comprising (1) a core, and (2) a coating comprising (a) a cladding of refractive index lower than said core and (b) a sensitive composition, wherein said sensitive composition changes optical properties upon interaction with said chemical and wherein said coating over said distributed region is essentially continuous and permeable to said chemical (B) providing light that is affected by said optical change in a manner that induces an optical change in the light guided by said fiber, and (C) monitoring said guided light.

17. The process of claim 16 wherein said chemical comprises oxygen.

18. The process of claim 17 wherein said sensitive material comprises 9,10-diphenylanthracene.

19. The process of claim 16 wherein said chemical comprises ammonia.

20. The process of claim 19 wherein said sensitive material comprises oxazine 750 perchlorate.

21. The process of claim 16 wherein said sensitive material is included in a cladding region of said coating.

22. The process of claim 16 wherein said sensitive material is included in a region of said coating surrounding a cladding region of said fiber.

23. The process of claim 16 wherein said sensitive material is located at the interface of said core and the cladding portion of said coating.

24. The process of claim 16 wherein said light that is affected by said optical change is provided transverse to said fiber.

25. The process of claim 24 wherein said sensitive material is included in a region of said coating comprising a cladding region of said coating.

26. The process of claim 24 wherein a fluorescent material that is affected by said optical change is located in said core.

27. The process of claim 16 wherein said light that is affected by said optical change is launched into said core.

28. The process of claim 16 wherein said monitored light emanates from said sensitive material and is subsequently guided by the fiber.

29. The process of claim 16 wherein said optical change results from a fluorescence quenching process.

30. The process of claim 16 wherein said optical change results from a scattering process.

31. The process of claim 16 wherein said optical change results from an optical absorption process.

* * * * *